United States Patent [19]

Seymour

[11] Patent Number: 5,380,492
[45] Date of Patent: Jan. 10, 1995

[54] SAMPLING DEVICE AND SAMPLE ADEQUACY SYSTEM

[76] Inventor: Eugene H. Seymour, 1465 Monaco Dr., Pacific Palisades, Calif. 90272

[21] Appl. No.: 47,713

[22] Filed: Apr. 14, 1993

Related U.S. Application Data

[63] Continuation-in-part of Ser. No. 889,283, Jun. 3, 1992, which is a continuation-in-part of Ser. No. 857,574, Mar. 24, 1992, abandoned, which is a continuation-in-part of Ser. No. 838,609, Feb. 19, 1992, Pat. No. 5,268,148, which is a continuation-in-part of Ser. No. 831,776, Feb. 5, 1992, Pat. No. 5,260,031, which is a continuation-in-part of Ser. No. 775,195, Oct. 11, 1991, Pat. No. 5,283,038, and Ser. No. 722,333, Jun. 25, 1991, abandoned, and Ser. No. 629,278, Dec. 18, 1990, abandoned.

[51] Int. Cl.⁶ .................... C12M 1/28; G01N 33/487
[52] U.S. Cl. .................... 422/101; 128/760; 422/58; 422/99; 435/294; 435/295
[58] Field of Search ............ 128/632, 760, 762, 769; 422/58, 99–102; 435/294–295

[56] References Cited

U.S. PATENT DOCUMENTS

| | | | |
|---|---|---|---|
| 3,620,677 | 11/1971 | Morison | 422/56 |
| 3,783,104 | 1/1974 | Henshilwood et al. | 435/295 |
| 3,966,558 | 6/1976 | Calva-Pellicer | 435/295 |
| 4,014,322 | 3/1977 | Shah | 128/760 |
| 4,014,746 | 3/1977 | Greenspan | 435/295 X |
| 4,150,950 | 4/1979 | Takeguchi et al. | 422/102 |
| 4,175,439 | 11/1979 | Laker | 604/1 X |
| 4,209,488 | 6/1980 | Breno | 422/101 |
| 4,425,320 | 1/1984 | Perry et al. | 422/101 X |
| 4,444,193 | 4/1984 | Fogt et al. | 422/58 X |
| 4,624,929 | 11/1986 | Ullman | 422/100 X |
| 4,635,488 | 1/1987 | Kremer | 128/760 |
| 4,678,757 | 7/1987 | Rapkin et al. | 422/56 X |
| 4,803,998 | 2/1989 | Kezes et al. | 435/295 X |
| 4,961,432 | 10/1990 | Guirguis | 128/760 |
| 4,999,285 | 3/1991 | Stiso | 422/58 X |
| 5,103,836 | 4/1992 | Goldstein et al. | 128/760 |

FOREIGN PATENT DOCUMENTS

| | | | |
|---|---|---|---|
| 2044422 | 1/1992 | Canada | 435/295 |
| 420450 | 4/1991 | European Pat. Off. | 435/295 |
| 63-293440 | 11/1988 | Japan | 128/760 |
| 2204398 | 11/1988 | United Kingdom | 422/56 |

Primary Examiner—James C. Housel
Assistant Examiner—Arlen Soderquist
Attorney, Agent, or Firm—W. Edward Johansen

[57] ABSTRACT

A saliva sampling device includes a sample container, a cap, a sample collector and a sample adequacy system. The sample container has an inner wall surface and a retaining ridge which is disposed on the inner wall surface. The sample collector includes a piece of filter paper and a holder which has a tube and a paddle coupled to the piece of filter paper. The paddle has a peripheral edge for engaging the retaining ridge of the sample container. The cap has an outer wall surface and an inner wall surface. The outer wall surface snugly engages the inner wall surface of the sample container. The inner wall surface has a truncated conical portion having a top and a cylindrical portion which is coupled to the truncated conical portion adjacent to the top thereof. The truncated conical portion thereof slidably engages the tube in order to guide the tube so that the cylindrical portion thereof snugly engages the tube.

2 Claims, 6 Drawing Sheets

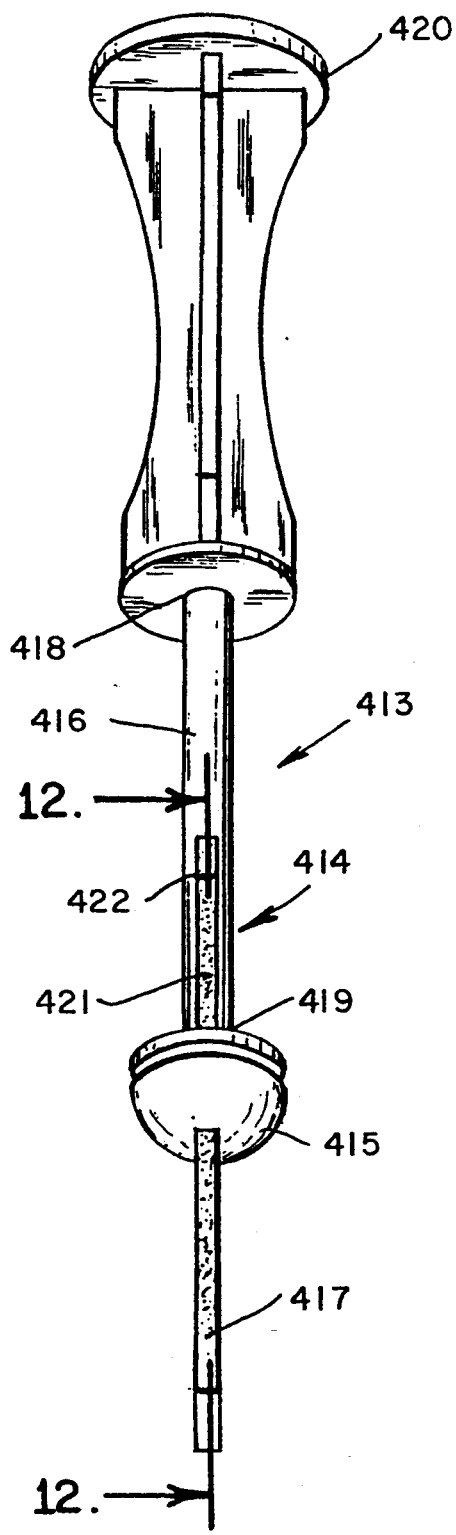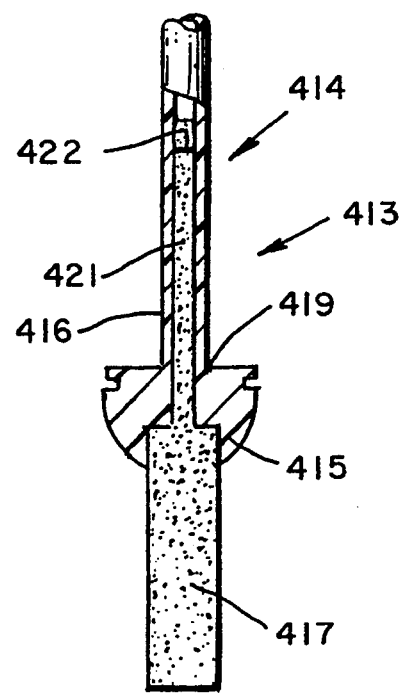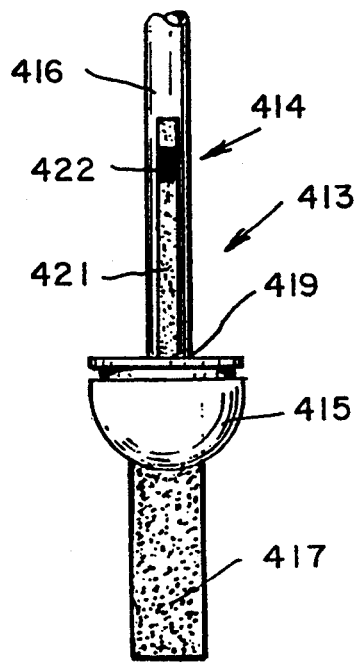

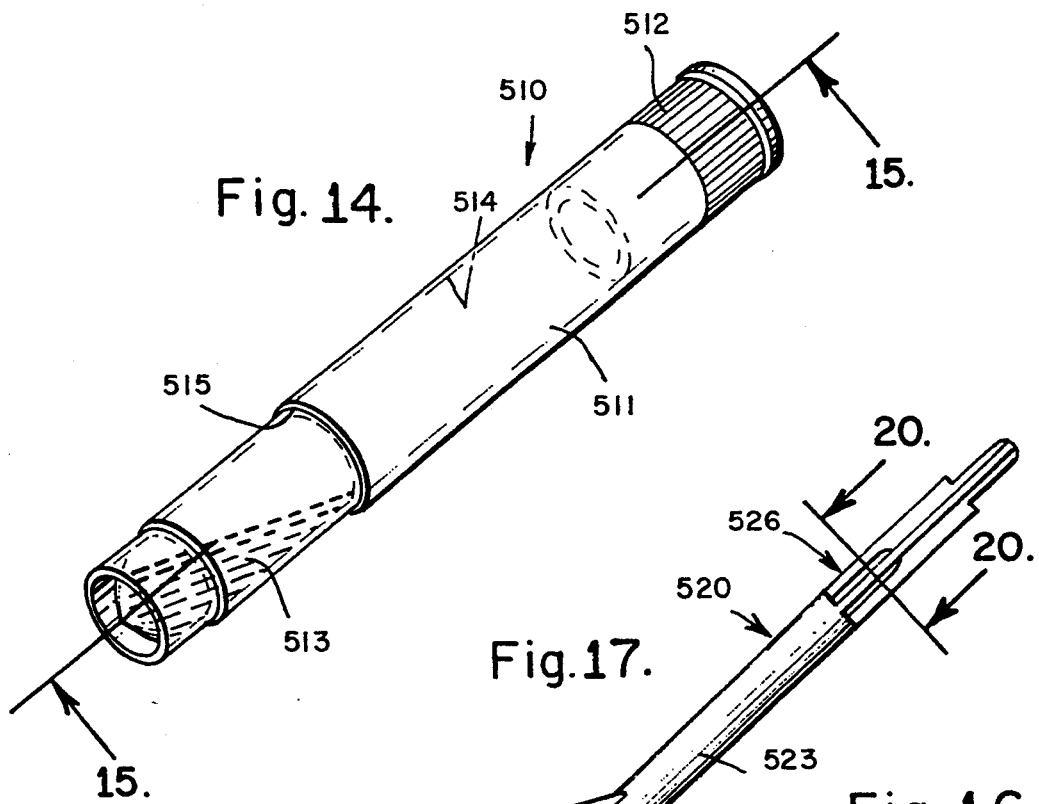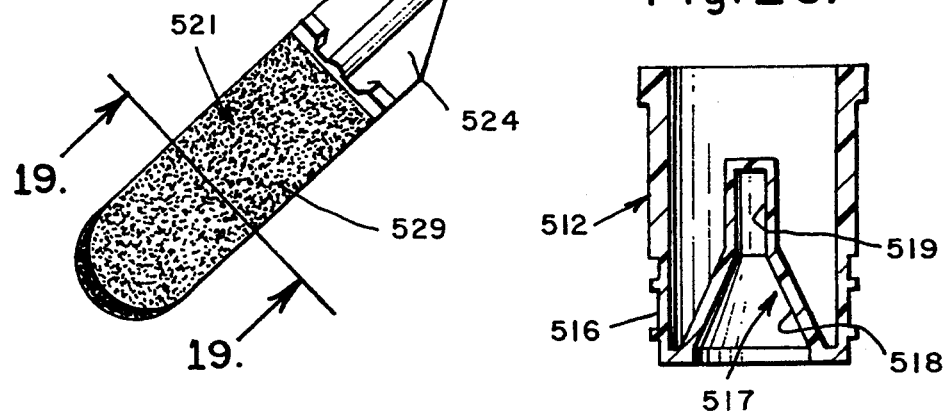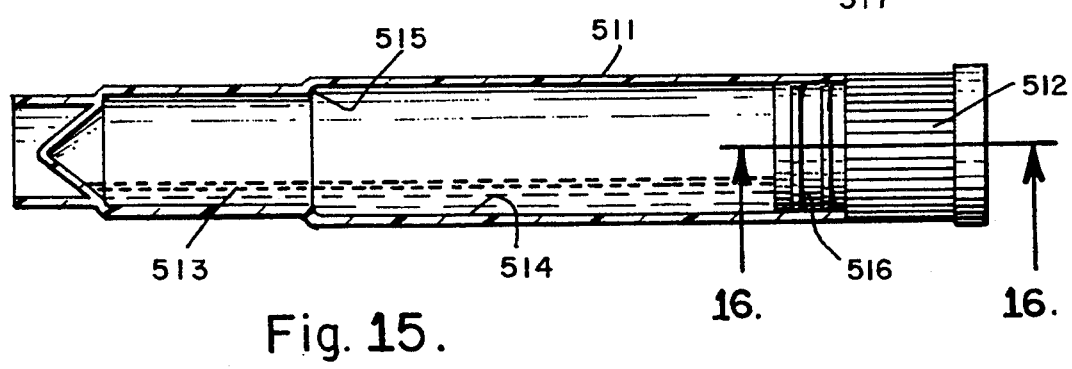

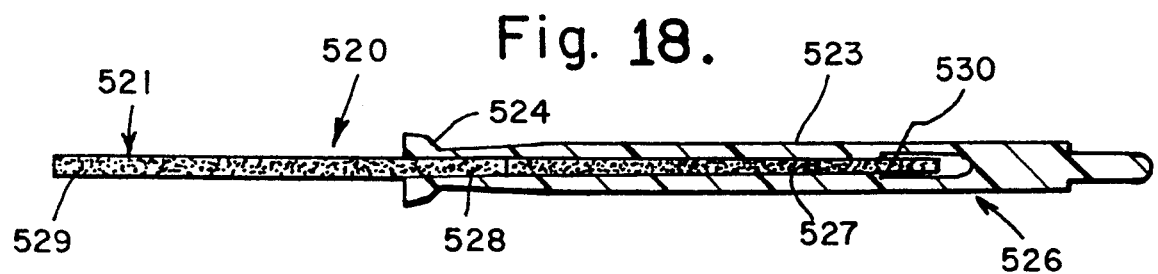
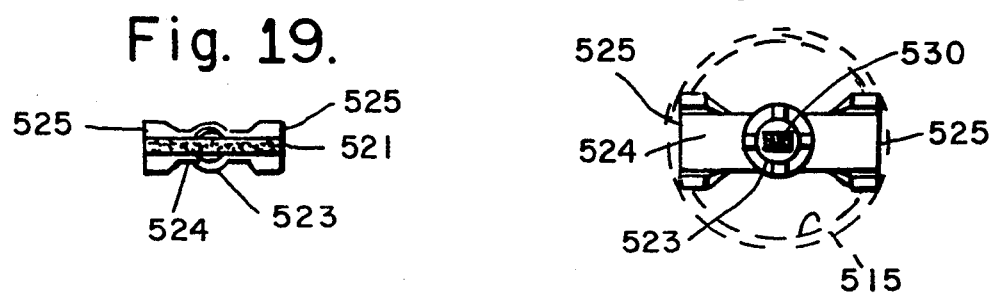
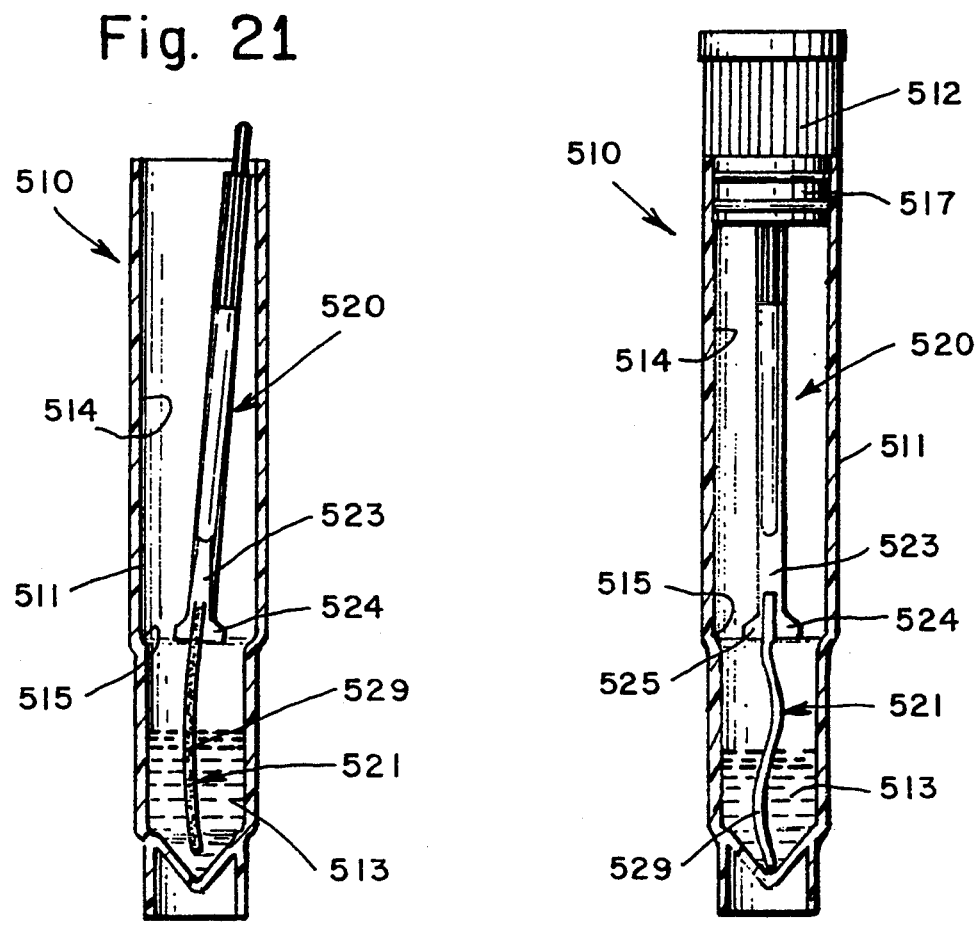

SAMPLING DEVICE AND SAMPLE ADEQUACY SYSTEM

This application is a continuation-in-part of the application filed Jun. 3, 1992 under Ser. No. 889,283; which is a continuation-in-part of the application filed Mar. 24, 1992 under Ser. No. 857,574, now abandoned which is a continuation-in-part of the application filed Feb. 19, 1992 under Ser. No. 838,609, now U.S. Pat. No. 5,268,148; which is a continuation-in-part of the application filed Feb. 5, 1992 under Ser. No. 831,776, now U.S. Pat. No. 5,260,031; which is a continuation-in-part of all of the application filed Oct. 11, 1991 under Ser. No. 775,195, now U.S. Pat. No. 5,283,038, the application filed Jun. 25, 1991 under Ser. No. 722,333, now abandoned, and the application filed Dec. 18, 1990 under Ser. No. 629,278, now abandoned, the disclosures of which are incorporated herein by reference.

BACKGROUND OF THE INVENTION

The field of the invention is saliva sampling devices.

The current literature indicates saliva is used to conveniently, easily, safely and effectively test an individual for a variety of medical conditions. These tests for medical conditions include a hepatitis screening for restaurant employees, HIV, continue (nicotine) and cocaine screening by insurance companies and an HIV antibody screening for medical purposes. Clinics for oncology, neurology, infertility, allergy, orthopedics and pain which had used urine, blood and serum samples to determine the medical conditions of their patients are now using samples of saliva for this same purpose.

U.S. Pat. No. 5,103,836 teaches a device for collecting immunoglobulins from the oral cavity for immunological testing. The device is a treated absorbent pad which is used to collect a specimen having a high concentration of immunoglobulins.

U.S. Pat. No. 4,150,950 teaches a sampling device which includes a container, a seal, a screw-cap, an elongated element and a specimen collector. The container has a liquid reagent which the seal seals into the bottom portion thereof capable of preserving the activity of a particular specimen. The specimen collector is attachable to the inside of the screw cap through the elongated element which is of sufficient length to immerse the specimen collector into the liquid. After a specimen has been obtained, the specimen collector, which is attached to the screw cap, is forced through the seal into the liquid preservative as the screw cap is fastened tightly onto the container.

SUMMARY OF INVENTION

The present invention is generally directed to a saliva sampling device which includes a sample container and a sample collector. The sample container has an inner wall surface. The sample collector includes a piece of filter paper and a holder having a tube and a paddle which is coupled to the piece of filter paper.

In a first separate aspect of the present invention, the sample container has a retaining ridge disposed on the inner wall surface. The holder has a peripheral edge for engaging the retaining ridge of the sample container.

In a second separate aspect of the present invention, the saliva sampling device also includes a cap which has an outer wall surface which snugly engages the inner wall surface of the sample container. The cap also has an inner wall surface which has a truncated conical portion having a top and a bottom and a cylindrical portion. The truncated conical portion is coupled to the cylindrical portion adjacent to the top thereof. The truncated conical portion thereof slidably engages the tube in order to guide said tube so that the cylindrical portion thereof snugly engages the tube.

In a third separate aspect of the present invention, the sample collector also includes an indicator. A first portion of the piece of filter paper is disposed within and coupled to the holder enclosed thereby, a second portion thereof is exposed and a third portion of the piece thereof is adjacent to the first portion thereof and disposed in the tube. The indicator is activated by a sample of saliva and is disposed in the third portion of the piece of filter paper. The indicator does not interfere with the collection of the sample of saliva. When the second portion of the piece of filter paper is inserted into a test subject's mouth saliva fluidly couples the second portion thereof to the indicator through the first and third portions thereof.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

BRIEF DESCRIPTION OF THE DRAWING

FIG. 11 is a perspective view of a sample collector.

FIG. 12 is an elevational view in a partial cross-section of the sample adequacy system of the sample collector of FIG. 11 before it has collected a sample taken along line 12—12 of FIG. 11.

FIG. 13 is an elevational view of the sample adequacy system of FIG. 11 after the sample collector has collected an adequate sample.

FIG. 14 is a perspective view of a saliva sampling device which includes a sample container and a cap according to the present invention.

FIG. 15 is a cross-sectional view of the saliva sample container of FIG. 14 taken along line 15—15 of FIG. 14.

FIG. 16 is a cross-sectional view of the cap of FIG. 14 taken along line 16—16 of FIG. 14.

FIG. 17 is a perspective view of a saliva collector of the saliva sampling device of FIG. 14 including a holder, a paddle and a piece of filter paper.

FIG. 18 is a longitudinal view in cross-section of the saliva collector of FIG. 17.

FIG. 19 is a transverse view in cross-section of the saliva collector of FIG. 17 taken along the line 19—19 of FIG. 17.

FIG. 20 is a transverse view in cross-section of the saliva collector of FIG. 17 taken along the line 20—20 of FIG. 17.

FIG. 21 is an elevational view in cross-section of the saliva sampling device of FIG. 14 without the cap thereof.

FIG. 22 is an elevational view in cross-section of the saliva sampling device of FIG. 14 with the cap thereof.

DESCRIPTION OF THE PREFERRED EMBODIMENT

Figure 1:
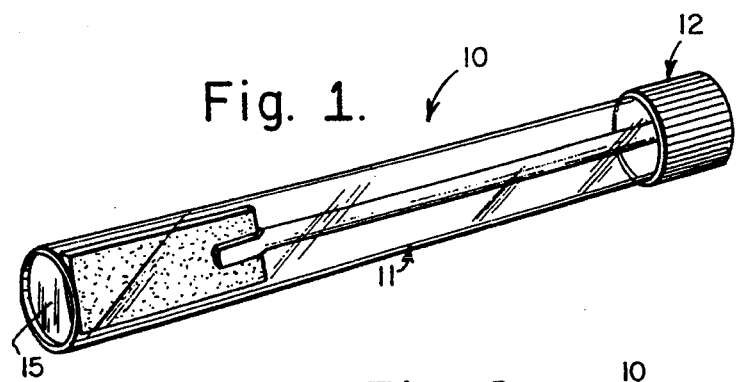
FIG. 1 is a perspective view of a saliva sampling device which includes a sample container and a saliva collector including a holder, an elongated member and a piece of filter paper.
Figure 2:
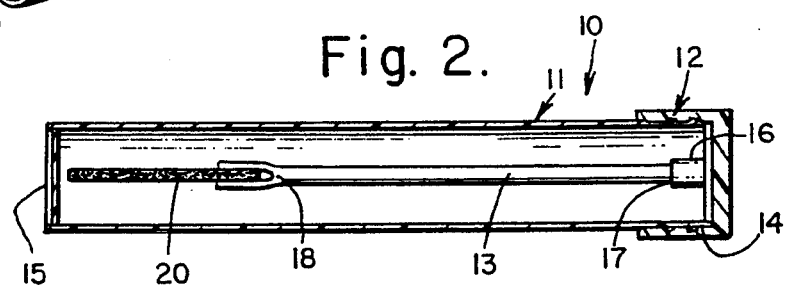
FIG. 2 is a side elevational view in cross-section of the saliva sampling device of FIG. 1.

Referring to FIG. 1 in conjunction with FIG. 2, a saliva sampling device 10 is used for collecting a measured sample of saliva. The saliva sampling device 10 includes a sample container 11, a cap 12 and a saliva collector 13, which is an elongated member. The sample container 11 has an open threaded end 14 and a closed end 15. The cap 12 has an inner surface 16 and is adapted to be mechanically coupled to the open threaded end 14 of the sample container 11 so that the cap 12 seals the sample container 11 air-tight. The saliva collector 13 has a first end 17 and a second end 18 with the first end 17 of which being mechanically coupled to the inner surface 16 of the cap 12. The saliva sampling device 10 also includes a piece of filter paper 20 which is of predetermined dimensions and which is mechanically coupled to the second end 18 of the saliva collector 13, so that a technician can collect a sample of saliva without touching the sample. Each sample of saliva is being collected wet and during the initial stages of testing of the saliva sampling device 10 a corresponding sample of blood serum is being compared thereto.

Figure 3:
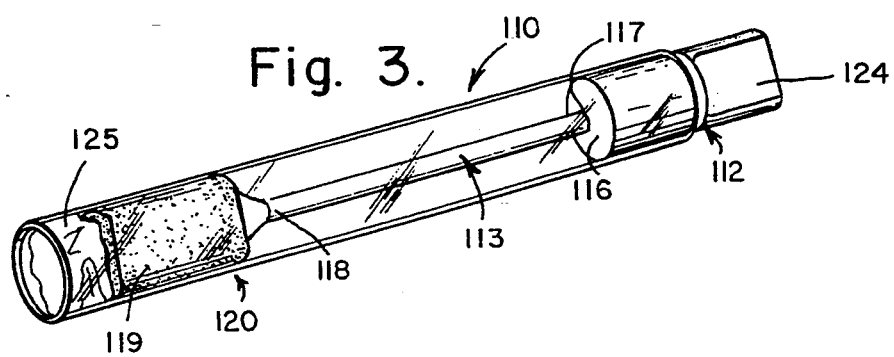
FIG. 3 is a perspective view of a saliva sampling device which includes a sample container and a saliva collector including a holder, a elongated member and a piece of filter paper.
Figure 4:
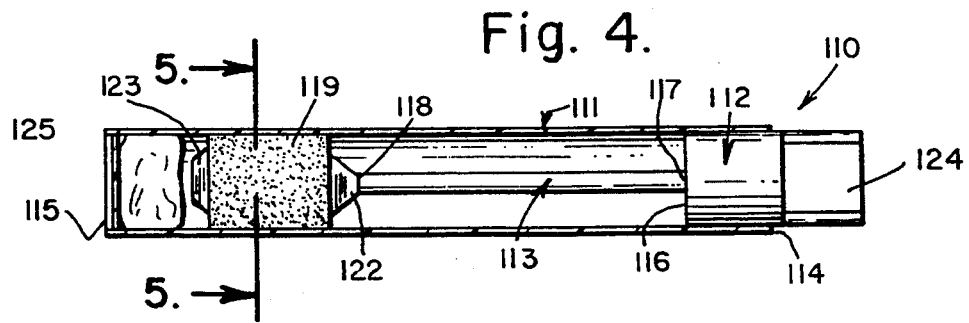
FIG. 4 is a side elevational view in cross-section of the saliva sampling device of FIG. 3.

Referring to FIG. 3 in conjunction with FIG. 4 a saliva sampling device 110 is used for collecting a measured sample of saliva. The saliva sampling device 110 includes a sample container 111, a plug 112 and a saliva collector 113, which is an elongated member. The sample container 111 has an open end 114 and a closed end 115. The plug 112 has an inner surface 116 and is adapted to be slidably coupled to the open end 114 of the sample container 111. The plug 112 seals the container 111 air-tight. The saliva collector 113 has a first end 117 and a second end 118. The first end 117 of the saliva collector 113 is mechanically coupled to the inner surface 116 of the plug 112.

Figure 5:
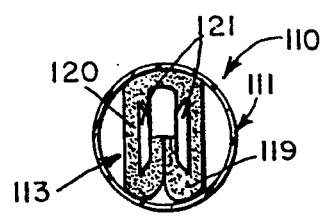
FIG. 5 is an end view in cross-section of the saliva sampling device of FIG. 3 taken along line 5—5 of FIG. 4.
Figure 6:
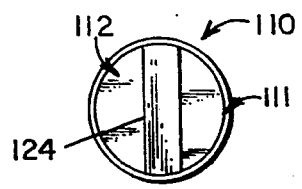
FIG. 6 is a top plan view of the saliva sampling device of FIG. 3.

Referring to FIG. 3 in conjunction with FIG. 4 and FIG. 5 the saliva sampling device 110 also includes a piece of filter paper 119 of pre-determined dimensions and a rectangular paddle assembly 120. The rectangular paddle assembly 120 includes two parallel and contiguous flat plates 121 each of which has a first end 122 and a second end 123 and which are joined together at their first ends 122 and mechanically coupled to the second end 118 of the saliva collector 113. The piece of filter paper 119 is mechanically coupled to the rectangular paddle assembly 120 so that a technician can collect the measured sample of saliva without touching the sample. The saliva sampling device 110 further includes a labeling mechanism 124 and a dessican 125. The labeling mechanism 124 labels the sample container 111 with the name of the patient and the date when the measured sample of saliva was taken. The dessican 125 removes the moisture content from the collected sample of saliva. The saliva sampling device 110 may also include a mailer which is used to transport the collected sample of saliva to a clinical laboratory for processing and analysis.

Figure 7:
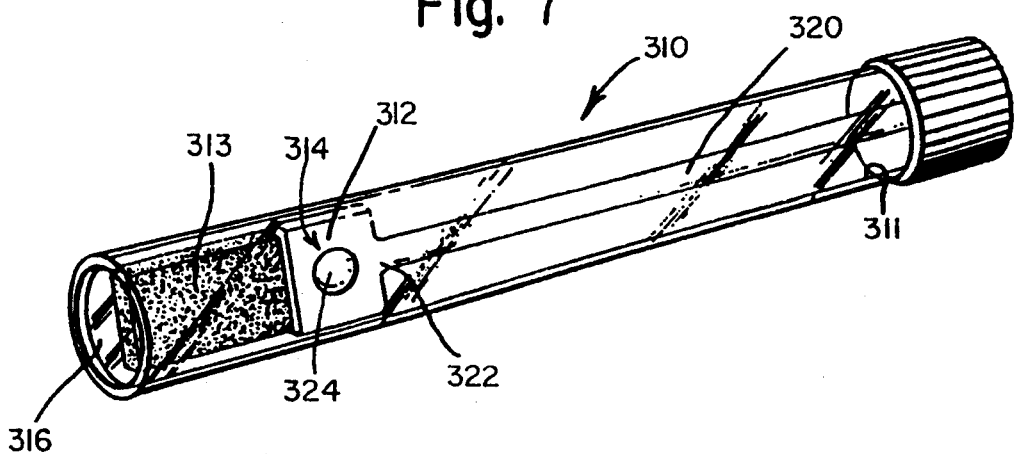
FIG. 7 is a perspective view of a saliva sampling device which includes a sample container, a saliva collector including a holder, a elongated member, a piece of filter paper and a sample adequacy system.
Figure 8:
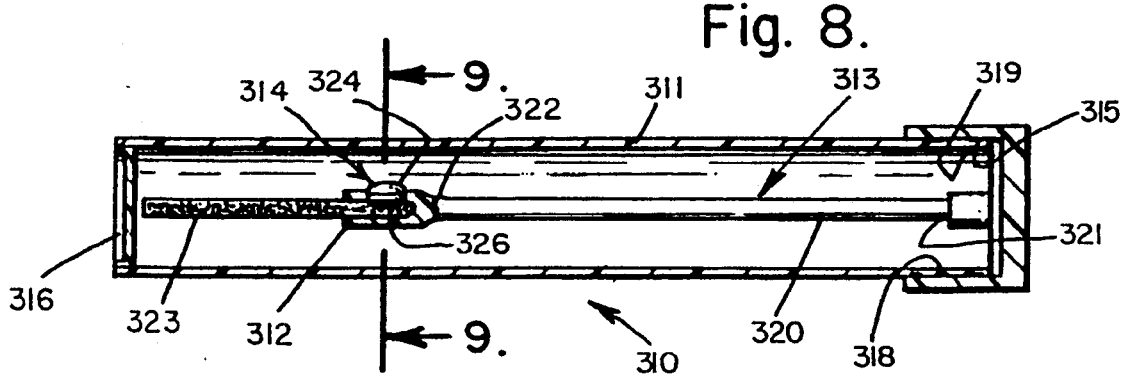
FIG. 8 is a longitudinal view in cross-section of the saliva sampling device of FIG. 7.

Referring to FIG. 7 in conjunction with FIG. 8 a saliva sampling device 310 includes a sample container 311, a holder 312, a saliva collector 313 and a sample adequacy system 314. The sample container 311 has an open threaded end 315 and a closed end 316. A solution 317 may be contained in the sample container 311. A cap 318 has an inner surface 319 and is coupled to the open threaded end 315 of the sample container 311 so that the cap 318 seals the sample container 311 air-tight. An elongated member 320 has a first end 321 and a second end 322. The first end 321 of the elongated member is coupled to the inner surface 319 of the cap 318. The holder 312 is coupled to the second end 322 of the elongated member 320. A piece of filter paper 323 is of predetermined dimensions and is mechanically coupled to the holder 312 so that a technician can collect a sample of saliva without touching the sample. The sample adequacy system 314 includes a plastic lens 324 and a hole 325 in the top surface of the holder 312 into which the plastic lens 324 is disposed. The top portion 326 of the piece of filter paper 323 is treated with a chemical reagent 327 which reacts with saliva by changing its color from a first color to a second color.

Figure 9:
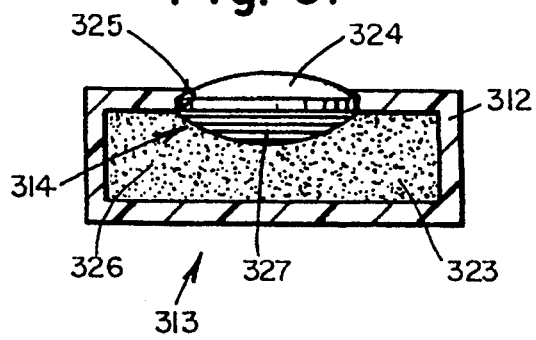
FIG. 9 is a cross-sectional view of the saliva collector of the saliva sampling device of FIG. 13 taken along line 9—9 of FIG. 8 showing the sample adequacy system before the saliva collector has been placed in a subject's mouth.
Figure 10:
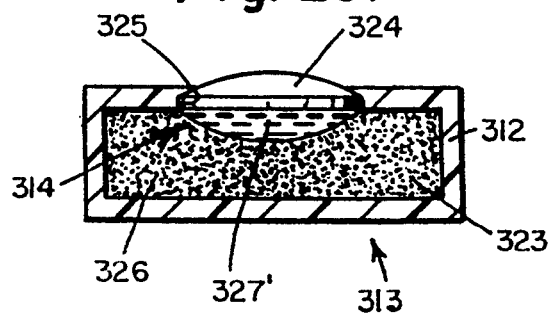
FIG. 10 is a cross-sectional view of the saliva collector of FIG. 7 taken along line 9—9 of FIG. 8 showing the sample adequacy system after the saliva collector has collected an adequate sample of saliva.

Referring to FIG. 7 in conjunction with FIG. 8, FIG. 9 and FIG. 10 before the saliva collector 313 has been placed in a subject's mouth the top portion 326 of the piece of filter paper 323 is of the color blue. When an adequate amount of saliva has been collected the saliva in the piece of filter paper 323 will reach the chemical reagent 327' and change the color blue to clear. Each sample of saliva will be collected wet and during the initial stages of testing of the saliva sampling device 310 a corresponding sample of blood serum is being compared thereto. Once an adequate amount of saliva has been collected the saliva the holder 312 and the piece of filter paper 320 are placed into the sample container 311 and shaken vigorously enough to separate the piece of filter paper 323 from the filter paper holder 319.

Referring to FIG. 11 in conjunction with FIG. 12 and FIG. 13 a sampling device also includes a sample collector 413 with a sample adequacy system 414. The sample collector 413 includes a piston-shaped holder 415, an elongated member 416 and a piece of filter paper 417. The elongated member 416 has a first end 418 and a second end 419. The first end 418 of the elongated member 416 is coupled to a push tab 420. The piston-shaped holder 415 is coupled to the second end 419 of the elongated member 416. The piece of filter paper 417 is of predetermined dimensions and is mechanically coupled to the piston-shaped holder 415 so that a technician can collect a sample without touching it. The sample adequacy system 414 is formed by an extension 421 of the filter paper 417 and either a drop of dye 422 or a line of ink placed at the top of the extension 421 of the filter paper 417. When an adequate amount of sample has been collected the drop of dye 422 mixes with a small amount of the collected sample causing the drop of dye 422 to bleed into a larger area at the top of the extension 421 of the filter paper 417. The sample collector 413 selectively receives a sample. The sample collector 413 can be used to collect samples of bodily fluids. These bodily fluids include saliva, urine, water, tears and vaginal fluids. The components of the sampling device 410 may be formed out of a plastic material which may be either opaque or non-opaque.

Referring to FIG. 14 in conjunction with FIG. 15 and FIG. 16 a saliva sampling device 510 includes a sample container 511, a cap 512 and a buffering solution 513. The sample container 511 has an inner wall surface 514 and a retaining ridge 515 which is disposed on the inner wall surface 514. The cap 512 has an outer wall surface 516 and an inner wall surface 517. The outer wall surface 516 of the cap 512 snugly engages the inner wall surface of the sample container. The inner wall surface 517 of the cap 512 has a truncated conical portion 518 having a top and a cylindrical portion 519 which is coupled to the truncated conical portion 518 adjacent to the top thereof.

Referring to FIG. 17 in conjunction with FIG. 18 and FIG. 19 the saliva sampling device 510 also includes a sample collector 520 which has a piece 521 of filter paper and a holder 522 which has a tube 523 and a paddle 524 coupled to the piece 521 of filter paper. The paddle 524 has a peripheral edge 525 for engaging the retaining ridge 515 of the sample container 511.

Referring to FIG. 17 in conjunction with FIG. 18 and FIG. 20 the saliva sampling device 510 further includes a sample adequacy system 526 having an indicator 527. The indicator is activated by a sample of saliva. The piece 521 of filter paper has a first portion 528, a second portion 529 and a third portion 530. The third portion 530 is disposed adjacent to the first portion 528. The first portion 528 is disposed within the paddle 524 enclosed thereby. The third portion is disposed in the tube 523 wherein the second portion 529 thereof is exposed. The indicator 527 is disposed in the third portion 530 so that the indicator 527 does not interfere with the collection of the sample of saliva. When the second portion 529 is inserted into a test subject's mouth saliva fluidly couples the second portion 529 to the indicator 527 through the first and third portions 528 and 530.

Referring to FIG. 21 in conjunction with FIG. 16, FIG. 17 and FIG. 22 when the sample collector 520 is placed in the sample container 511 the peripheral edge 525 of the paddle 524 engages the retaining ridge 515 of the sample container 511 so that the paddle 524 does not contact the buffering solution 513. When the truncated conical portion 518 of the cap 512 slidably engages the tube 523 the cylindrical portion 519 thereof snugly engages the tube 523.

Figure 23:
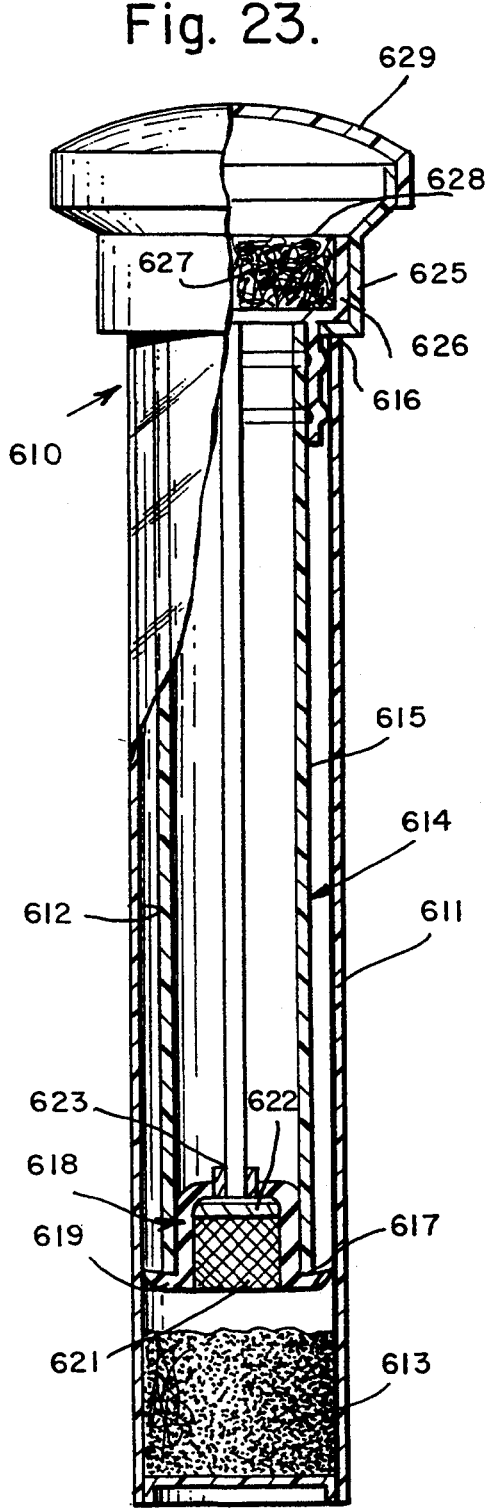
FIG. 23 is an elevational view in partial cross-section of the saliva testing device which has a separating device.

Referring to FIG. 23 a saliva testing device 610 includes a sample container 611 having an inner wall surface 612, a piece 613 of filter paper and a separating device 614. The piece 613 of filter paper contains a saliva sample. The separating device 614 includes a hollow piston 615, which has a first open end 616 and a second open end 617, and a cylindrical, rubber gasket 618 which is snugly disposed in the second end 617. The cylindrical, rubber gasket 618 is slidably coupled to the sample container 611. The cylindrical, rubber gasket 618 has a flange 619, a first opening 620 into which a filter 621 and a conjugate disc 622 are placed and a second opening 623. The filter 621 and the first and second openings 620 and 623 are used in separating the saliva sample from the piece 613 of filter paper. The separating device 614 is used to press the saliva sample from the sample container 611 into the hollow piston 615. U.S. Pat. No. 4,895,808 teaches a test tube and tube-like adsorption column. The sample to be analyzed is prepared in solution and placed in the test tube. The tube-like adsorption column which has a seal and a valve member is forcefully fed into the test tube to force solutions through the valve member into the column and through a filter.

Figure 24:
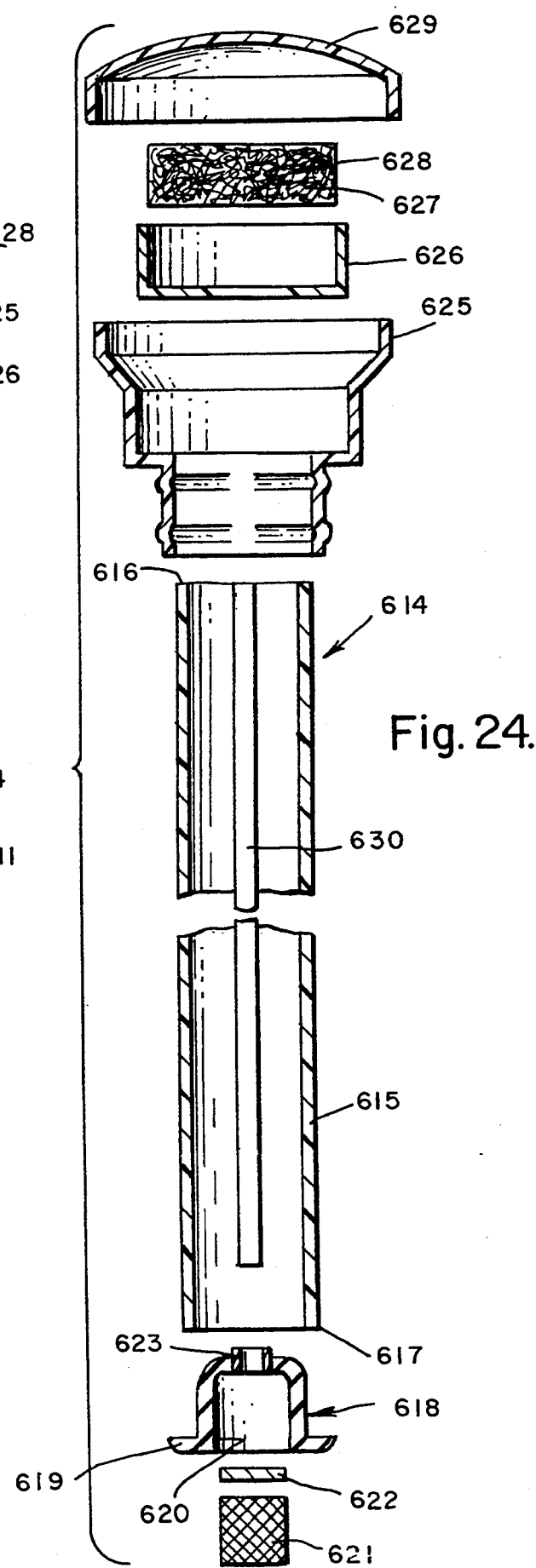
FIG. 24 is an exploded, elevational view in cross-section of the saliva testing device of FIG. 23.

Referring to FIG. 24 in conjunction with FIG. 23 the saliva testing device 610 also includes a cap base 625, an absorbent shell 626, an absorbent mass 627, a membrane 628 and a cap window 629 and a wicking tube 630. The cap base 625 is snugly coupled to the sample container 611. The absorbent shell 626 is disposed in the cap base 625. The absorbent mass 627 is disposed in the absorbent shell 626. The membrane 628 covers the absorbent mass 627 and has been treated with a chemical agent. The cap window 629 is coupled to the cap base 625 and covers the membrane 628. The wicking tube 630 is fluid coupled to the absorbent shell 626. When the separating device 614 squeezes out the saliva sample into the hollow piston 615 the wicking tube 630 transports the saliva sample to the absorbent mass 627 through the absorbent shell 626 so that an analytical test of the saliva sample can be performed on the membrane 628. The results of the analytical test can be seen on the membrane 628 through the cap window 629.

From the foregoing it can be seen that a saliva sampling device has been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:
1. A saliva sampling device comprising:
 a. a sample container having an open end, a closed end and an inner wall surface;
 b. a retaining ridge disposed on said inner wall surface adjacent to said closed end; and
 c. a sample collector including a piece of filter paper and a holder having a tube and a paddle coupled to said piece of filter paper, said paddle having a peripheral edge for engaging said retaining ridge of said sample container thereby preventing said paddle from being inserted into said sample container beyond said retaining ridge.
2. A saliva sampling device according to claim 1 wherein said saliva sampling device also includes a cap having an outer wall surface which snugly engages said inner wall surface of said sample container and an inner wall surface having a truncated conical portion which has a top and a cylindrical portion which is coupled to said truncated conical portion adjacent to said top thereof whereby said truncated conical portion thereof slidably engages said tube in order to guide said tube so that said cylindrical portion thereof snugly engages said tube.

* * * * *